(12) United States Patent
Moeller

(10) Patent No.: US 10,453,373 B2
(45) Date of Patent: Oct. 22, 2019

(54) PROGRESSIVE DISPLAY ALTERATION IN REAL-TIME TO EFFECT DESIRABLE BEHAVIOR

(71) Applicant: Posture Solutions, LLC, St. Louis, MO (US)

(72) Inventor: Trent Moeller, St. Louis, MO (US)

(73) Assignee: Posture Solutions, LLC, St. Louis, MO (US)

( * ) Notice: Subject to any disclaimer, the term of this patent is extended or adjusted under 35 U.S.C. 154(b) by 0 days.

(21) Appl. No.: 15/851,959

(22) Filed: Dec. 22, 2017

(65) Prior Publication Data

US 2018/0190175 A1    Jul. 5, 2018

Related U.S. Application Data

(60) Provisional application No. 62/440,137, filed on Dec. 29, 2016.

(51) Int. Cl.
*G09G 3/20* (2006.01)
*G06T 11/00* (2006.01)
(Continued)

(52) U.S. Cl.
CPC ......... *G09G 3/2003* (2013.01); *A61B 5/4561* (2013.01); *G06F 3/0346* (2013.01); *G06T 11/001* (2013.01); *G06T 11/60* (2013.01); *G09G 2320/0261* (2013.01); *G09G 2320/068* (2013.01); *G09G 2320/0666* (2013.01); *G09G 2340/12* (2013.01); *G09G 2340/14* (2013.01); *G09G 2354/00* (2013.01); *G09G 2380/08* (2013.01)

(58) Field of Classification Search
USPC ......................................................... 345/592
See application file for complete search history.

(56) References Cited

U.S. PATENT DOCUMENTS 8,441,343 B1    5/2013 Fishman
9,141,761 B2    9/2015 Lee
(Continued)

FOREIGN PATENT DOCUMENTS

JP    2014-006932 A    1/2014
KR    10-2011-0093464 A    8/2011
KR    10-1445228 B1    9/2014

OTHER PUBLICATIONS

Search Report of related International Application PCT/US2017/068084 dated Apr. 18, 2018, 5 pgs.
(Continued)

*Primary Examiner* — Wesner Sajous
(74) *Attorney, Agent, or Firm* — Stinson LLP

(57) ABSTRACT

Altering a display of visual information in real time on an electronic visual display of a mobile computing system to encourage desirable behavior, such as spinal posture. In an embodiment, a system determines an angle of inclination of a mobile computing system, which is indicative of a spinal posture of a user of the system. When the user's spinal posture is within an angular range that corresponds to a less desirable spinal posture, the system progressively alters a display of visual information by an electronic visual display of the system to encourage the user toward a more desirable spinal posture.

20 Claims, 15 Drawing Sheets

(51) Int. Cl.
*G06T 11/60* (2006.01)
*A61B 5/103* (2006.01)
*A61B 5/00* (2006.01)
*G06F 3/0346* (2013.01)

(56) References Cited

U.S. PATENT DOCUMENTS

| | | | |
|---|---|---|---|
| 9,177,457 B2 | 11/2015 | Shin et al. | |
| 2013/0072820 A1* | 3/2013 | Lee | A61B 5/1071 600/594 |
| 2014/0022369 A1 | 1/2014 | Kwon | |
| 2014/0088607 A1* | 3/2014 | Recknor | A61B 5/6898 606/102 |
| 2016/0089272 A1 | 3/2016 | Li et al. | |
| 2016/0132173 A1 | 5/2016 | Kim | |
| 2017/0227841 A1* | 8/2017 | Niemela | G02B 13/06 |
| 2019/0042838 A1* | 2/2019 | Bose | H04N 7/18 |

OTHER PUBLICATIONS

Written Opinion of related International Application PCT/US2017/068084 dated Apr. 18, 2018, 6 pgs.
The Text Neck Institute, the Text Neck Indicator: A Mobile App, retrieved from https://web.archive.org/web/20161116195758/http://text-neck.com/text-neck-indicator-a-mobile-app.html, Nov. 16, 2016.
Sawh, Michael, Alex posture tracker first look: The wearable that wants to end 'text neck', retrieved from https://web.archive.org/web/20161026122348/http://www.wareable.com:80/health-and-wellbeing/alex-posture-tracker-review, Oct. 26, 2016.
Adams, Derek, Sit up straight: Best smart posture trainers to save your back, retrieved from https://web.archive.org/web/20161116171000/https://www.wareable.com/wearable-tech/the-best-wearables-for-improving-your-posture, Nov. 16, 2016.

* cited by examiner

US 10,453,373 B2

PROGRESSIVE DISPLAY ALTERATION IN REAL-TIME TO EFFECT DESIRABLE BEHAVIOR

CROSS-REFERENCE TO RELATED APPLICATION

This application claims priority from U.S. Provisional Patent Application Ser. No. 62/440,137, filed Dec. 29, 2016, the entire contents of which are expressly incorporated herein by reference, including the contents and teachings of any references contained therein.

FIELD

Aspects of the present invention relate to the field of mobile computing devices for effecting desirable behavior, such as desired user spinal posture, in real time.

BACKGROUND

Clinical studies indicate that large percentages of mobile device users are developing poor spinal posture habits from tilting their heads forward when viewing visual displays on the mobile device. The load/strain put on the spine from poor spinal posture habits leads to spinal problems, such as development of a straight cervical spine. Conventional techniques to address this problem utilize a binary approach that merely indicates on which side of a threshold the user's spinal posture is located. But the risk of bad spinal posture increases significantly below about sixty degrees and these binary approaches do not convey to users the urgency of correcting spinal posture as it deviates farther from the threshold. Other conventional approaches merely generate a small (e.g., less than 25% of the screen) notification of the user's spinal posture, which fails to induce desirable behavior from the user.

Another conventional approach includes an eyeglass-like apparatus that functions as a blinder. However, disadvantages of this approach include lack of adoption due to the apparatus not always being located nearby the user and dependence on user honesty to actually wear the apparatus. Moreover, the apparatus occludes the wearer's field of vision for all tasks while wearing the apparatus such that the wearer must manually remove the apparatus to regain full vision (e.g., for conversing with others, viewing important messages, viewing important environmental cues, etc.).

SUMMARY

Aspects of the invention relate to progressively altering a display of visual information on mobile computing devices in real time when the device detects less desirable behavior of the user of the device. For example, when an angle of inclination of the device indicates a less desirable spinal posture of the user of the device. In an embodiment, an operating system, software development kit, and/or application executing on the device equates an angle of inclination of the device with a spinal posture of the user and progressively alters the display of visual information in real time to encourage desirable spinal posture. In an embodiment, altering the display includes displaying a non-disruptive frame around the visual information to note less desirable spinal posture and affirm more desirable spinal posture. In another embodiment, altering the display includes progressively obfuscating the visual information to prevent effective use of the device with less desirable spinal posture.

A system embodying aspects of the invention includes an electronic visual display, an orientation sensor, a processor, and a memory device. The processor is communicatively coupled to the electronic visual display and the orientation sensor. The memory device stores processor-executable instructions. When executed by the processor, the instructions configure the processor to receive signals indicative of an angle of inclination of the system from the orientation sensor and compare the angle of inclination of the system with a predetermined angular range. The predetermined angular range corresponds to a less desirable cervical spinal posture of a user of the system. The instructions also configure the processor to determine the user has the less desirable cervical spinal posture when the angle of inclination of the system is within the predetermined angular range. And the instructions configure the processor to alter a display of visual information by the electronic visual display in real time when the user of the system has the incorrect cervical spinal posture.

A method embodying aspects of the invention includes a processor of a mobile computing device executing processor-executable instructions. The executing instructions receive signals indicative of an angle of inclination of a mobile computing device from an orientation sensor and compare the angle of inclination of the device with a predetermined angular range. The predetermined angular range corresponds to a less desirable cervical spinal posture of a user of the mobile computing device. The executing instructions further determine the user has the less desirable behavior when the angle of inclination of the mobile computing device is within the predetermined angular range and alter a display of visual information on an electronic visual display of the mobile computing device in real time when the user has the less desirable behavior.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
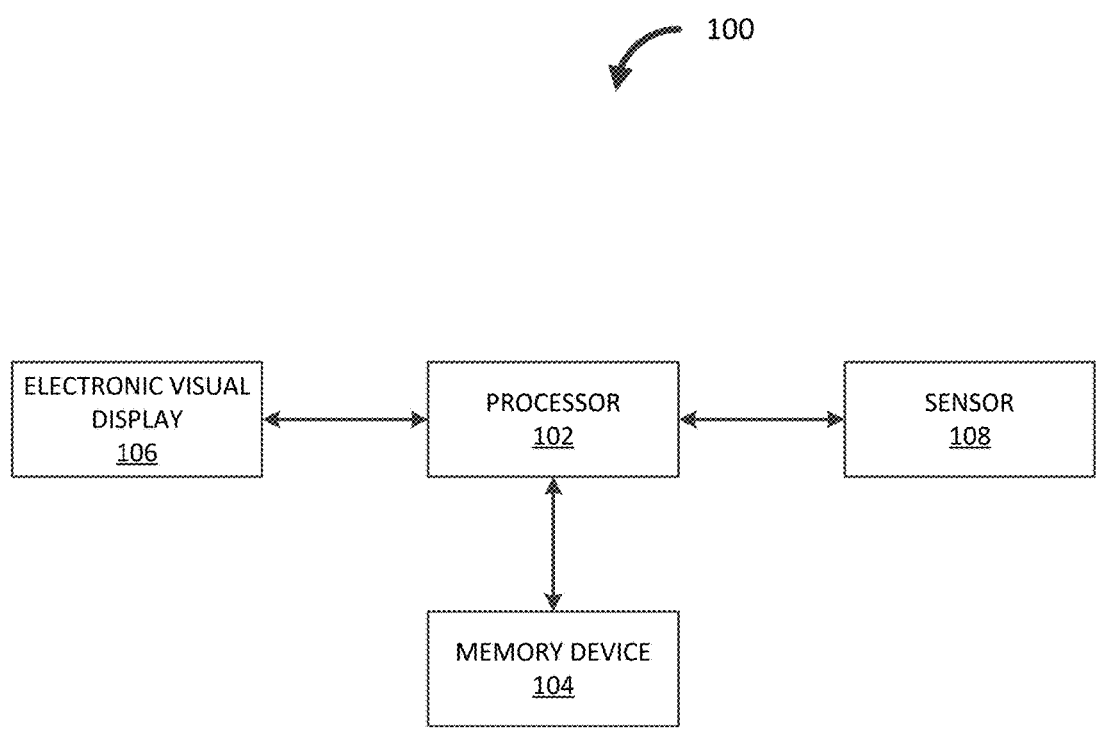
FIG. 1 is a block diagram of an mobile computing device system according to an embodiment.

FIG. 1 illustrates an exemplary mobile computing device system, generally indicated at 100, in accordance with an aspect of the invention. The system 100 includes a processor 102, a memory device 104, an electronic visual display 106, and a sensor 108. The mobile computing device system may be a mobile phone, a tablet computing device, a smartphone, and the like.

The memory device 104 is configured to store processor-executable instructions that comprise at least one of an operating system, a software development kit (SDK), and an application that monitor and track a spinal posture of the user when executed by processor 102. In an embodiment, memory device 104 is configured to store an angular range that corresponds to a less desirable spinal posture of a user of system 100. The angular range may be predetermined and embodied in the processor-executable instructions or may be entered by a user via the electronic visual display 106. In an embodiment, the predetermined angular range comprises a twenty degree range having a maximum value at any point between twenty degrees and ninety degrees. For example, a user of system 100 and/or a caretaker of the user can change the starting degree of the twenty-degree angular range based on the user's needs and/or goals.

The sensor 108 is configured to determine the orientation of system 100 and provide a real-time indication of the orientation to processor 102. For example, sensor 108 may be a gyroscope, an accelerometer, a camera, and the like. In an embodiment, sensor 108 is internal to system 100 (e.g., sensor 108 utilizes a power source of system 100). In another embodiment, sensor 108 is external to system 100. For example, sensor 108 may be integrated with a case or holder for system 100 (e.g., sensor 108 utilizes its own power source).

As described more fully herein, processor 102 receives the real-time angle of inclination of system 100 from sensor 108, compares the angle of inclination to the angular range stored in memory device 104, determines the user has a less desirable spinal posture when the angle of inclination is within the angular range, and alters a display of visual information by electronic visual display 106 when the user has the less desirable spinal posture.

In an embodiment, memory device 104 stores data representative of behavior patterns of a user of system 100. For example, memory device 104 may store an angle of inclination of system 100 for each application executed by processor 102. Specifically, usage of system 100 is tracked in ten degree increments and may be graphically displayed on electronic visual display 106 by using the same colors as the notification frames (described more fully herein). These statistics may be displayed by electronic visual display 106 per each day and/or calendar date range. The statistics may also be displayed by electronic visual display 106 for each application executed by processor 102 (e.g., social media applications, gaming applications, etc.). Moreover, the electronic visual display 106 can display statistics for other users of the spinal posture operating system, SDK, and application and filter the statistics by state, city, application, gender, age, and the like. In an embodiment, electronic visual display 106 displays a rank of the user compared to other users from similar categories.

Figure 2:
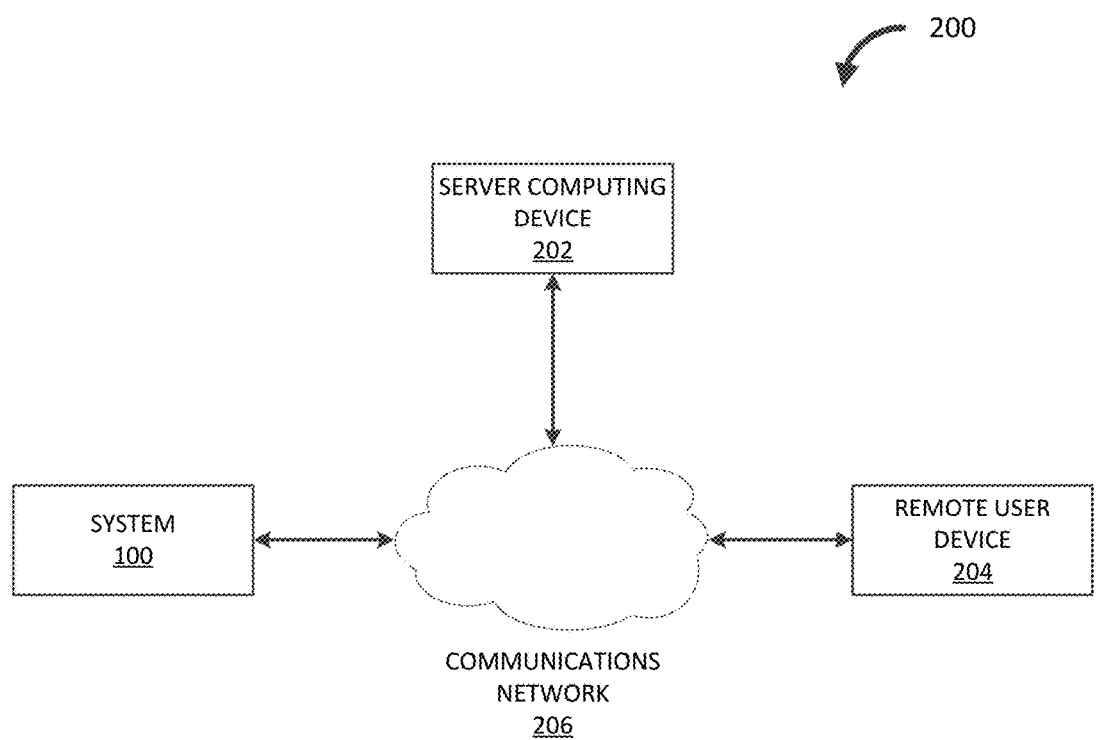
FIG. 2 is a block diagram of a posture tracking system according to an embodiment.

FIG. 2 illustrates an exemplary posture tracking system, generally indicated at 200, in accordance with an aspect of the invention. The posture tracking system 200 includes system 100, a server computing device 202, a remote user device 204, and a communications network 206.

In an embodiment, the communications network 206 is capable of facilitating the exchange of data among various components of posture tracking system 200. The communications network 206 may include a local area network (LAN) that is connectable to other telecommunications networks, including other LANs or portions of the Internet or an intranet. The communications network 206 may also be any telecommunications network that facilitates the exchange of data, such as those that operate according to the IEEE 802.3 (e.g., Ethernet) and/or the IEEE 802.11 (e.g., Wi-Fi) protocols, for example. In other embodiments, the communications infrastructure is any medium that allows data to be physically transferred through serial or parallel communication channels (e.g., copper wire, optical fiber, computer bus, wireless communication channel, etc.).

In an embodiment, the server computing device 202 is configured to store the data representative of behavior patterns of the user of system 100 and/or other users. The server computing device 202 enables system 100 to display statistics for other users of the spinal posture operating system, SDK, and application and display a rank of the user of system 100 compared to other users from similar categories, as further described herein. In an embodiment, server computing device 202 communicates (e.g., transmits and receives data) with system 100 via communications network 206. The user's statistics may be used to award badges or medals or to otherwise gamify the system.

In an embodiment, the remote user device 204 enables a caretaker (e.g., parent, guardian, healthcare professional, etc.) of a user of system 100 to provide the acceptable angular range for the user of system 100. For example, the caretaker may enter the angular range and remote user device 204 may transmit the range directly to system 100 via communications network 206 and/or to server computing device 202 via communications network 206 for later transmission to system 100. In another embodiment, the remote user device 204 displays (e.g., via its own electronic visual display) the data representative of the behavior patterns of the user of system 100 and/or other users for monitoring compliance, ranking users, etc. The remote user device 204 may be a mobile phone, a tablet computing device, a smartphone, a desktop computing device, a laptop computing device, a smartwatch, and the like.

Figure 3A:
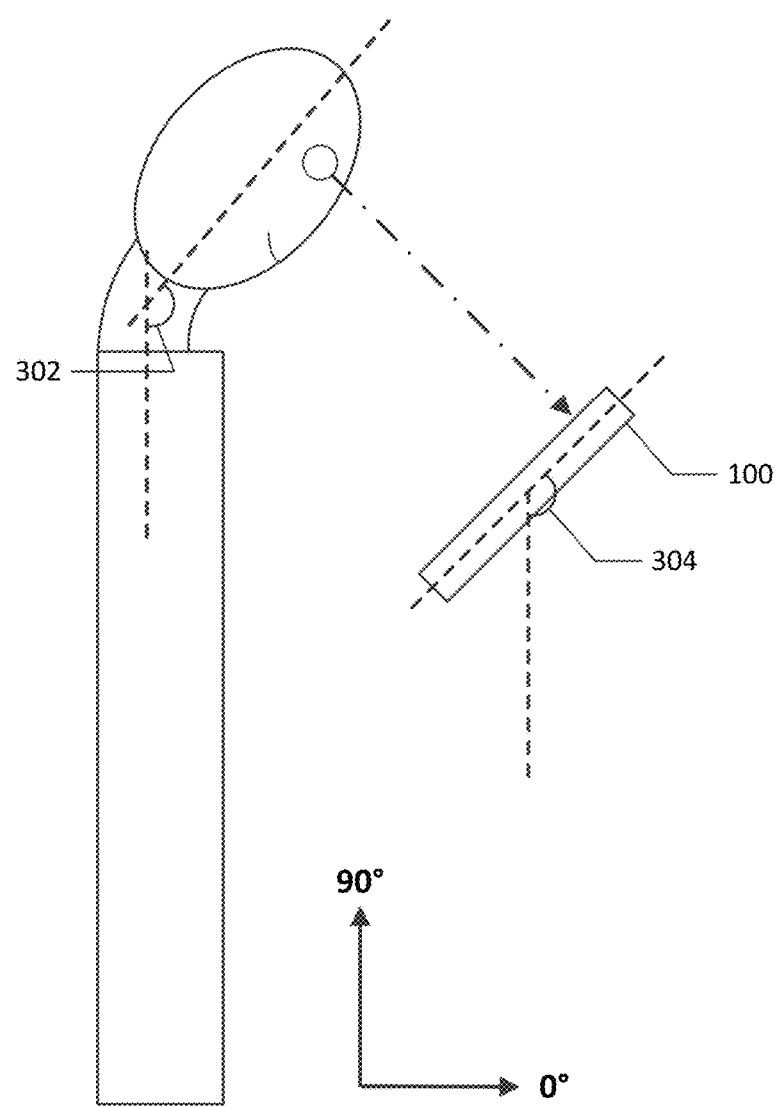
FIGS. 3A and 3B illustrate exemplary inclination angle concepts for use with the system of FIG. 1 and/or the system of FIG. 2 according to an embodiment.
Figure 3B:
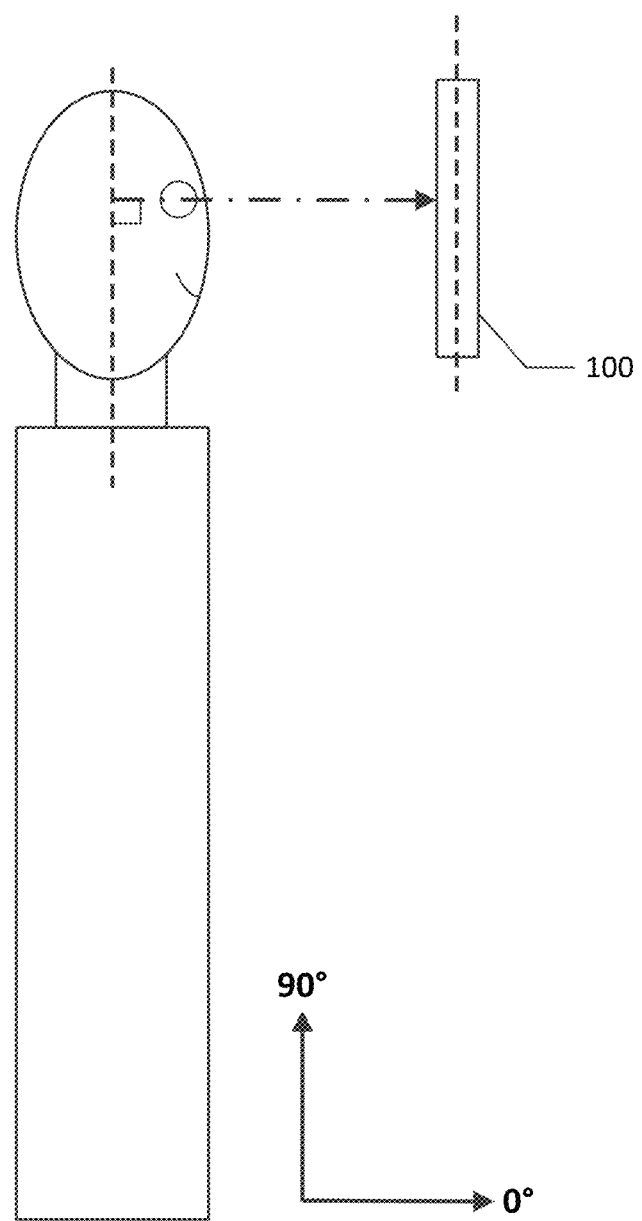

FIG. 3A illustrates the correspondence between a degree of inclination of system 100 and a degree of tilt of the user's neck. As illustrated, the degree of tilt of the user's neck 302 generally mimics the degree of inclination 304 of system 100 while the user is sitting or standing (i.e., as goes the tilt of system 100, so goes the tilt of the user's head). An operating system, SDK, and/or application executing on system 100 in accordance with an embodiment of the invention operate under the assumption that an inclination of ninety degrees (FIG. 3B) is the best angle for reducing the load/strain on the user's cervical, thoracic, and/or lumbar spine, and an inclination of zero degrees is the worst angle for the load/strain on the user's spine. Furthermore, the risk to the user increases significantly and in a more extreme manner below sixty degrees. Therefore, the sense of urgency to encourage posture correction increases significantly as the angle of inclination of system 100 approaches zero degrees.

Figure 4:
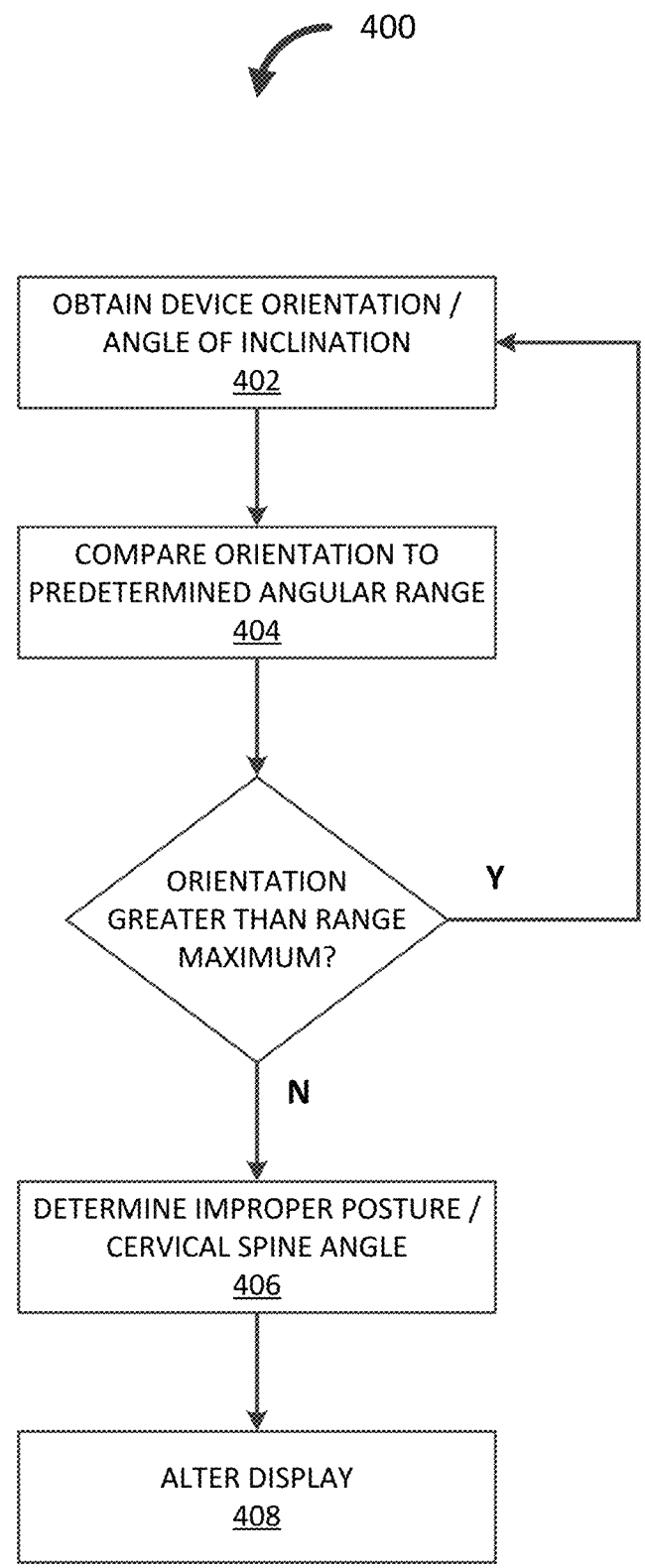
FIG. 4 is an exemplary flowchart of a real-time process for altering a display of visual information on an electronic visual display based on user posture according to an embodiment.

FIG. 4A illustrates an exemplary real-time process 400 for altering a display of visual information on electronic visual display 106 based on user posture. At step 402, processor 102 obtains the orientation (e.g., angle of inclination) of system 100 from sensor 108. The processor 102 compares the received angle of inclination of system 100 to the predetermined angular range stored in memory device 104 at step 404. When the angle of inclination of system 100 is greater than a maximum of the predetermined angular range it is indicative of a more desirable user spinal posture and the process returns to step 402. When the angle of inclination of system 100 is less than a maximum of the predetermined angular range it is indicative of a less desirable user spinal posture. At step 406, processor 102 determines the improper posture/spine angle of the user of system 100. The processor 102 then alters a display of visual information by electronic visual display 106 at step 408 based on the determined improper posture/spine angle of the user compared to the predetermined angular range.

Figure 5:
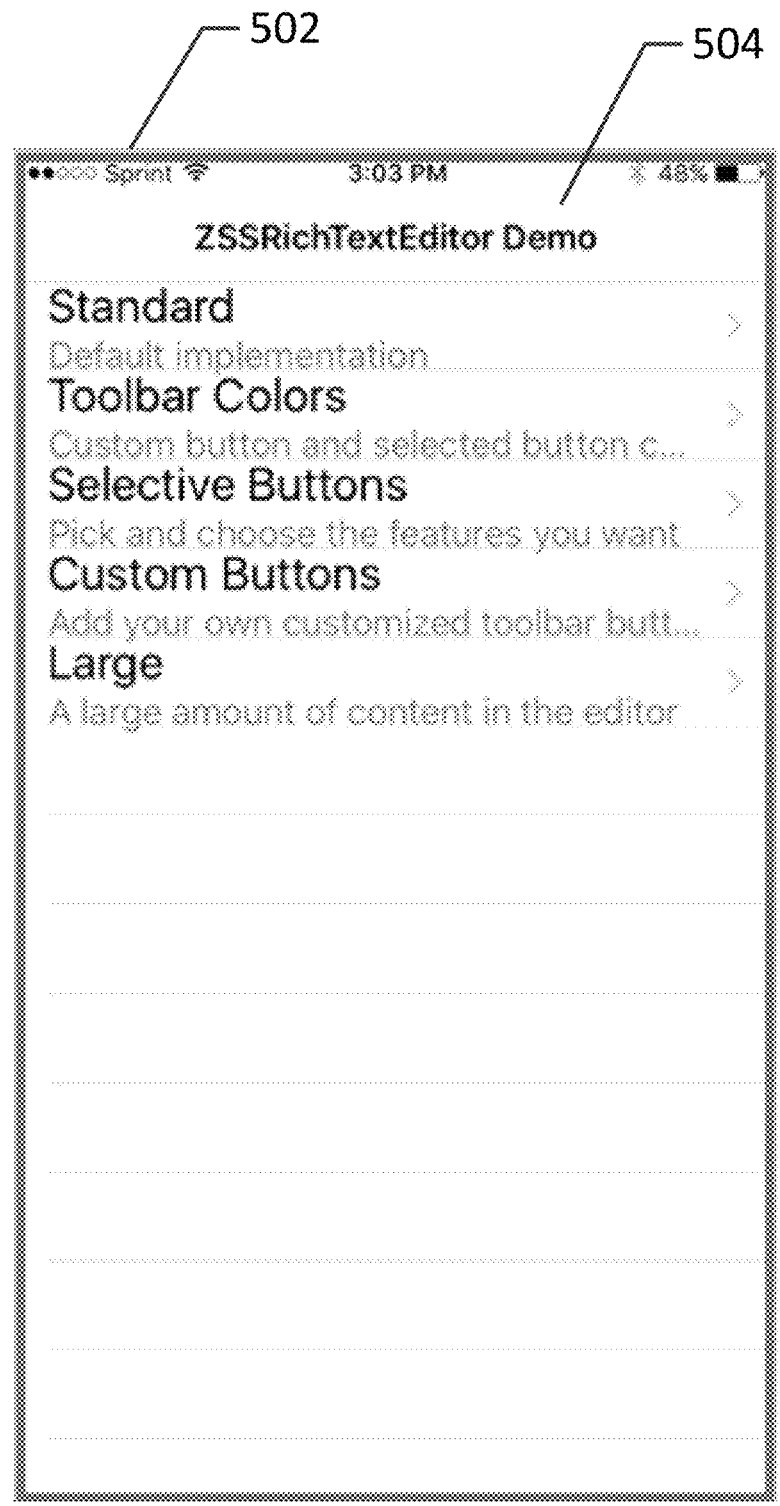
FIGS. 5 and 6 are exemplary screenshots illustrating an alteration of a display of visual information via notification frames according to an embodiment.

In an embodiment, step 408 comprises electronic visual display 106 displaying a notification frame. In an exemplary embodiment illustrated by FIG. 5, electronic visual display 106 may display a notification frame 502 around a content area 504. In an embodiment, the notification frame 502 progressively (i.e., non-binary) changes colors as the angle of inclination of system 100 progressively decreases from ninety degrees towards zero degrees.

In an exemplary and non-limiting embodiment, electronic visual display 106 displays a green notification frame 502 around the content area 504 when the angle of inclination of system 100 is between 81 and 90 degrees, a yellow notification frame 502 around the content area 504 when the angle of inclination of system 100 is between 70 and 74 degrees, and a red notification frame 502 around the content area 504 when the angle of inclination of system 100 is between 55 and 64 degrees. Moreover, the green notification frame 502 pulses at a rate of two pulses per second when the angle of inclination of system 100 is between 75 and 80 degrees, the yellow notification frame 502 pulses at a rate of two pulses per second when the angle of inclination of system 100 is between 65 and 69 degrees, and the red notification frame 502 begins pulsing at a rate of two pulses per second when the angle of inclination of system 100 is at 54 degrees and increases to pulsing at a rate of ten pulses per second when the angle of inclination of system 100 is at zero degrees. In an embodiment, the pulse rate increases from two pulses per second to ten pulses per second because the risk of increased load/strain on the user's cervical, thoracic, and lumbar spine increases significantly below sixty degrees and thus the sense of urgency to encourage posture correction increases significantly as the angle of inclination of system 100 approaches zero degrees. In an embodiment, a first color (e.g., red) of notification frame 502 notes poor user posture, a second color (e.g., yellow) of notification frame 502 notes average user posture, and a third color (e.g., green) of notification frame 502 affirms good user posture.

Figure 6:
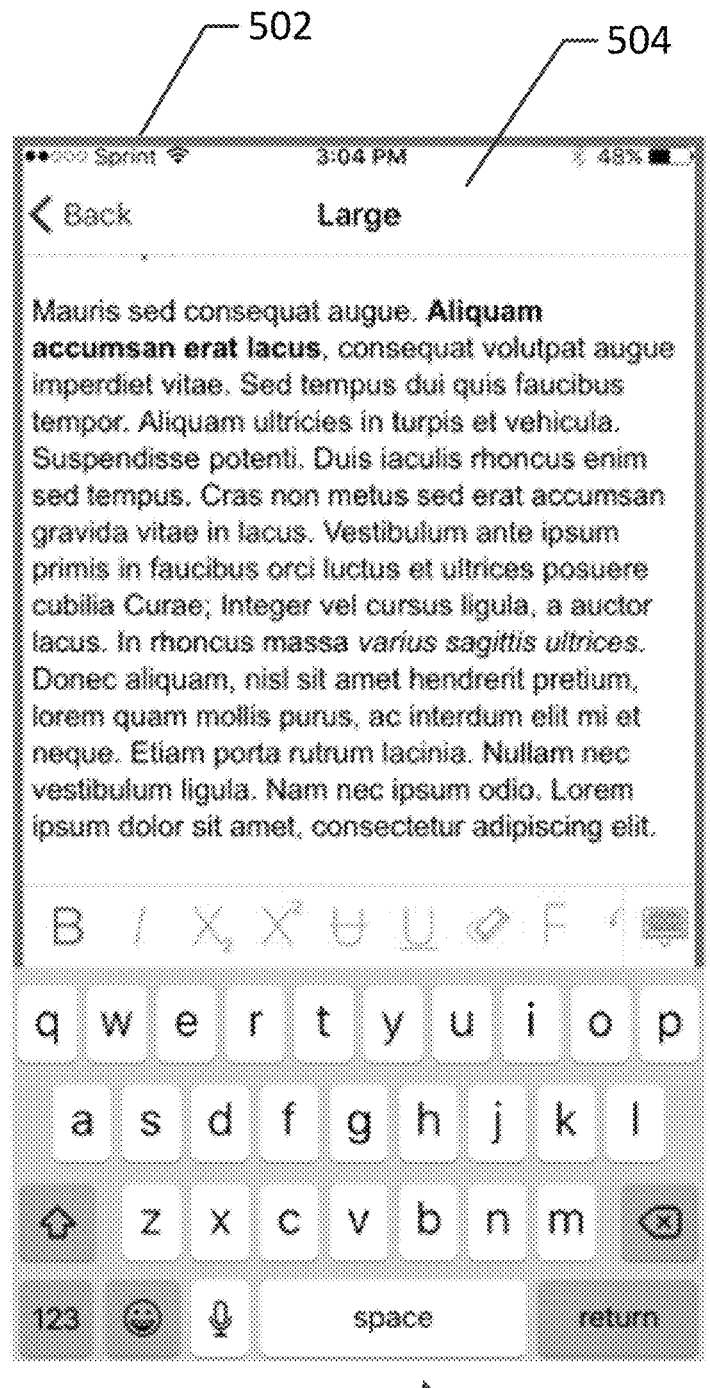

In an embodiment, notification frames 502 do not disrupt the display of content area 504 by electronic visual display 106. In other words, no functions of the operating system and/or application executing on system 100 are slowed or impaired in any manner. As illustrated by the exemplary embodiment of FIG. 6, the notification frame 502 does not impair usage of a user input component (e.g., keypad, etc.) 602. In an embodiment, processor 102 reduces the size of content area 504 to accommodate the notification frame 502. For example, if the normal content area is 4 inches by 6 inches (4"×6"), processor 102 reduces the dimensions to 4"×6" less the size of notification frame 502. In another embodiment, notification frames 502 are translucent overlays atop content area 504.

In another embodiment, the notification frame 502 progressively (i.e., non-binary) becomes thicker and fills in content area 504 as the angle of inclination of system 100 progressively decreases from ninety degrees towards zero degrees. For example, the thickness of notification frame 502 may increase from about seven points to about fifteen points as the angle of inclination of system 100 decreases from fifty five degrees to zero degrees in accordance with an embodiment. In yet another embodiment, system 100 vibrates each time notification frame 502 transitions from one color to another and/or from a non-pulsating state to a pulsing state. For example, vibration of system 100 may become increasingly more intense as the angle of inclination of system 100 (and thus the spinal posture of the user) progressively decreases from ninety degrees towards zero degrees. In another embodiment, system 100 triggers a vibration on an external wearable device, such as a smartwatch (e.g., Apple Watch) and the like. Advantageously, utilizing an external vibrating device would reduce battery usage of system 100. The vibration pattern of system 100 and/or an external device may be constant after the angle of inclination of system 100 is below fifty degrees or may increase intensity for every ten degrees approaching zero degrees in accordance with one or more embodiments. An exemplary vibration intensity pattern includes:

Vibrate once every 5 seconds between 66°-70°
Double vibration every 5 seconds between 61°-65°
Double vibration every 3 seconds between 56°-60°
Double vibration every 2 seconds between 51°-55°
Constant vibration between 0°-50°.

Figure 7:
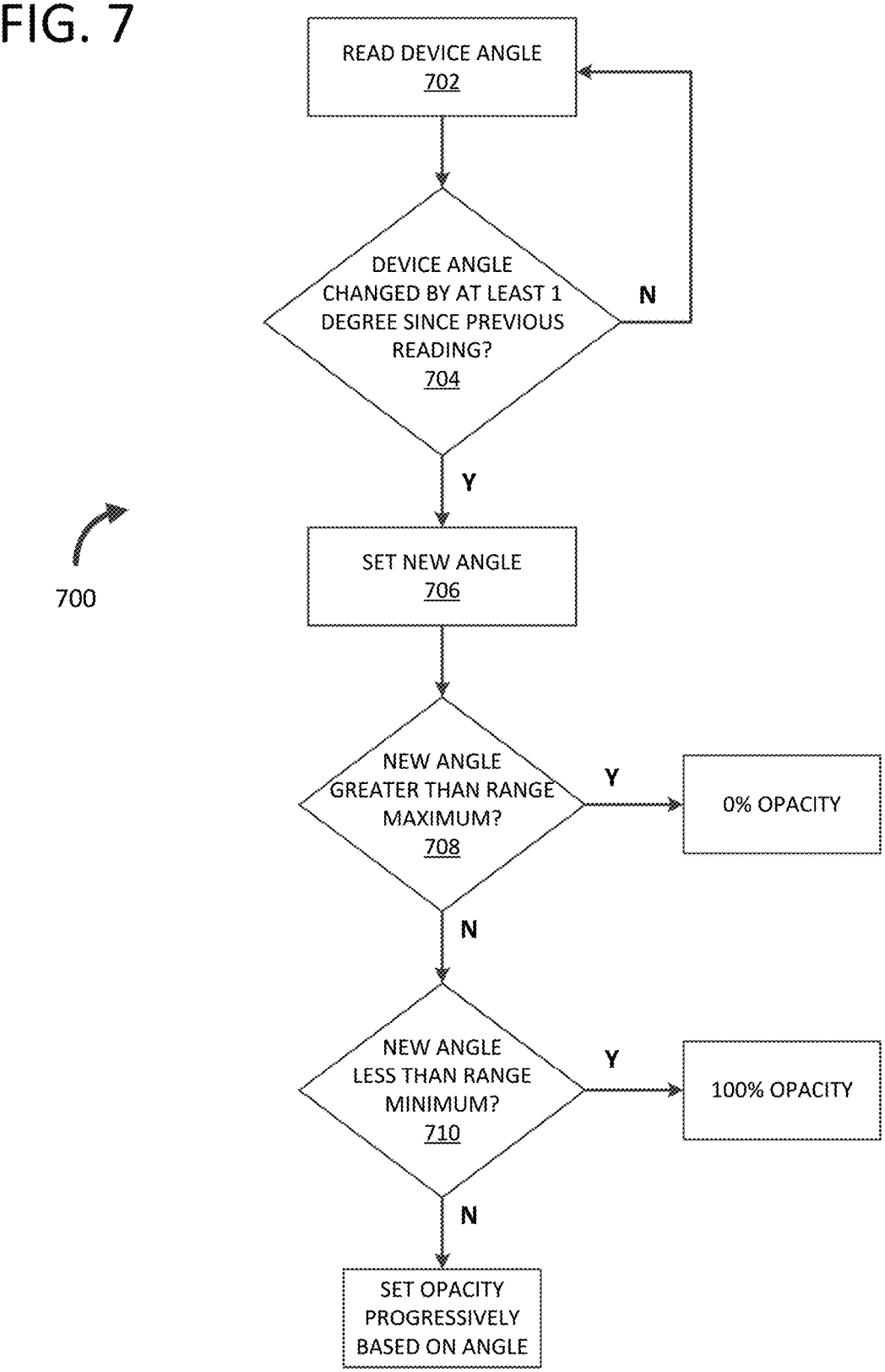
FIG. 7 is an exemplary flowchart of a real-time process for obfuscating a display of visual information on an electronic visual display based on user posture according to an embodiment.

FIG. 7 illustrates an exemplary real-time process 700 for obfuscating a display of visual information on electronic visual display 106 based user posture. In an embodiment, the real-time obfuscation of visual information displayed on electronic visual display 106 prevents a user from effectively using system 100 (e.g., mobile device) when the user's head is tilted forward in a less desirable spinal posture. At step 702, processor 102 reads the angle of inclination of system 100 from sensor 108. In an embodiment, processor 102 reads the angle at a predetermined interval (e.g., once every millisecond, once every second, etc.). The processor determines, at step 704, whether the angle of inclination obtained at step 702 differs by at least one degree from a previous device angle stored in memory device 104. When the device angle has not changed by at least one degree, the process continues back to step 702. When the device angle changes by one degree or more, processor 102 writes this new angle of inclination to memory device 104 at step 706.

Figure 8:
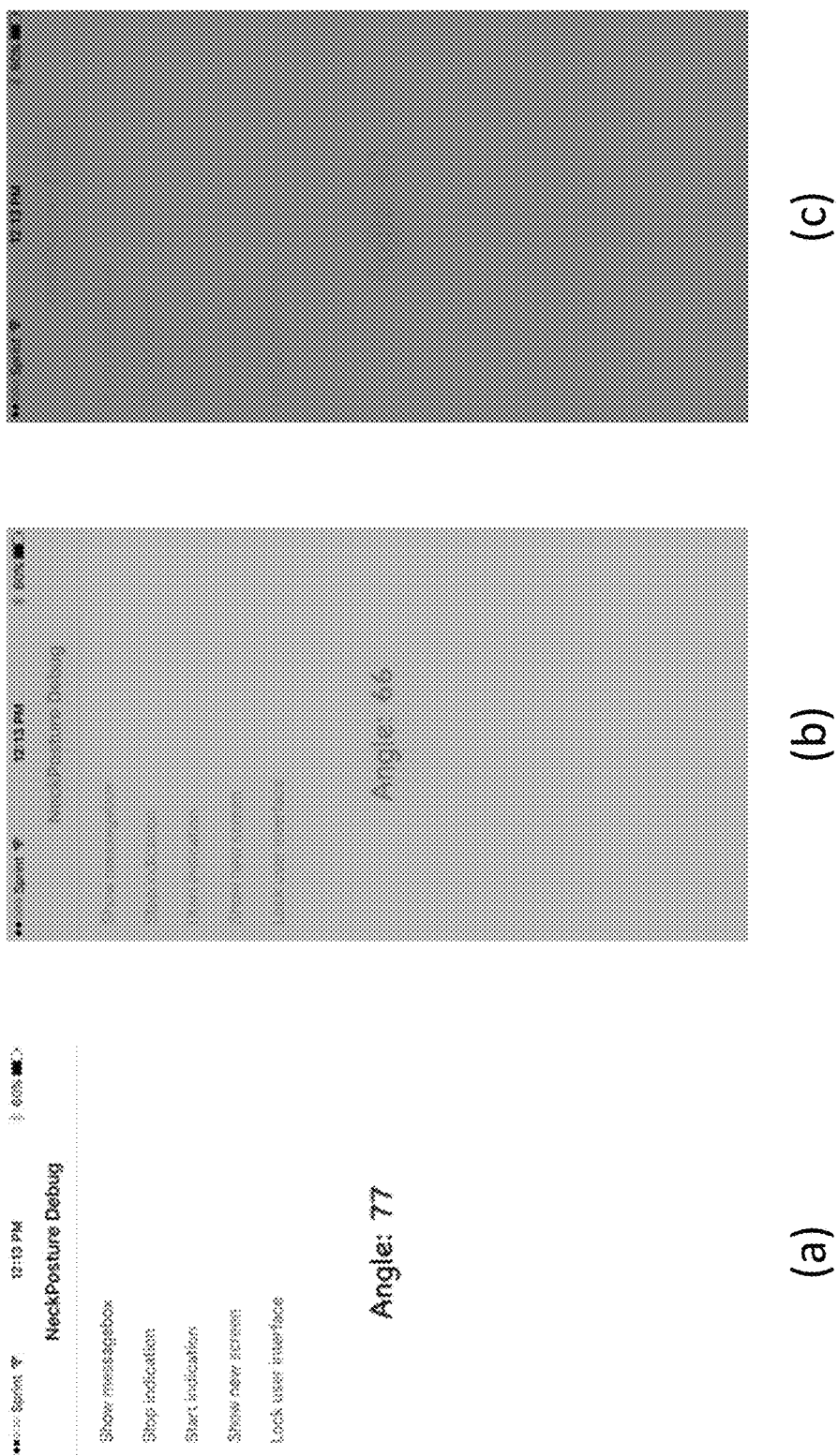
FIGS. 8, 9, and 10A-10E are exemplary screenshots illustrating an obfuscation of a display of visual information via a gray overlay screen according to an embodiment.

At step 708, processor 102 determines whether the new angle of inclination is greater than a maximum value of the predetermined angular range stored in memory device 104. When the angle of inclination of system 100 is greater than the maximum value of the predetermined angular range, processor 102 sets the opacity of an overlay screen to zero percent (i.e., the overlay screen is one hundred percent transparent). In an embodiment, the overlay screen is a gray screen, as described more fully hereinafter. In another embodiment, the overlay screen is any image desired by the user (e.g., a "Devolution of Man" image, etc.). Frame (a) of FIG. 8 illustrates an exemplary embodiment in which the overlay screen has an opacity of zero percent when the angle of inclination of system 100 is 77 degrees. In this exemplary embodiment, the overlay screen has an opacity of zero percent when the angle of inclination of system 100 is between 90 degrees and 76 degrees. Referring again to FIG. 7, the process continues to step 710 when the angle of inclination of system 100 is less than or equal to the maximum value of the predetermined angular range.

At step 710, processor 102 determines whether the new angle of inclination is less than a minimum value of the predetermined angular range stored in memory device 104. When the angle of inclination of system 100 is less than the minimum value of the predetermined angular range, processor 102 sets the opacity of the overlay screen to one hundred percent (i.e., the overlay screen is zero percent transparent).

Frame (c) of FIG. 8 illustrates an exemplary embodiment in which the overlay screen has an opacity of one hundred percent when the angle of inclination of system 100 is less than about 55 degrees.

Referring again to FIG. 7, when the angle of inclination of system 100 is greater than or equal to the minimum value of the predetermined angular range and less than or equal to the maximum value of the predetermined angular range, processor 102 sets the opacity of the overlay screen based on the angle of inclination of system 100. In an embodiment, the opacity of the overlay screen progressively (i.e., non-binary) increases as the angle of inclination of system 100 progressively decreases from the maximum value of the predetermined angular range towards the minimum value of the predetermined angular range. Frame (b) of FIG. 8 illustrates an exemplary embodiment in which the overlay screen has an opacity of about fifty percent when the angle of inclination of system 100 is about 66 degrees. In this exemplary embodiment, the opacity of the overlay screen progressively increases at a rate of about five percent per angle as the angle of inclination of system 100 decreases from 75 degrees to 55 degrees.

The real-time obfuscation of visual information in accordance with process 700 occurs over a twenty degree range. The degree at which the obfuscation begins may be chosen by the user and/or a caretaker of the user. The twenty degree range can start anywhere from ninety degrees to twenty degrees. No matter where the obfuscation begins, it will be completely opaque when it reaches the end of the twenty degree range.

Figure 9:

Although embodiments described herein include obfuscation of 100% of the total area of visual information, embodiments in which about 25% or more (i.e., less than 100%) of the total area of visual information is obfuscated are within the scope of the present disclosure. FIG. 9 illustrates exemplary embodiments in which less than 100% of the total area of visual information is obfuscated. For example, frame (a) illustrates about 25% obfuscation, frame (b) illustrates about 50% obfuscation, and frame (c) illustrates about 75% obfuscation. In the embodiments utilizing less than 100% obfuscation, the area of obfuscation may be located at any position within the area of visual information. For example, the area of obfuscation may be located directly in the center of the area of visual information, along one or more sides of the area of visual information, based on importance of the underlying visual information (e.g., the obfuscation is placed atop visual information having higher importance to the user, etc.), or the like. Moreover, the area of obfuscation may be discontinuous (e.g., stripes, chevron pattern, polka-dot, etc.) such that areas of obfuscation are interwoven with areas of visual information.

Figure 10A:
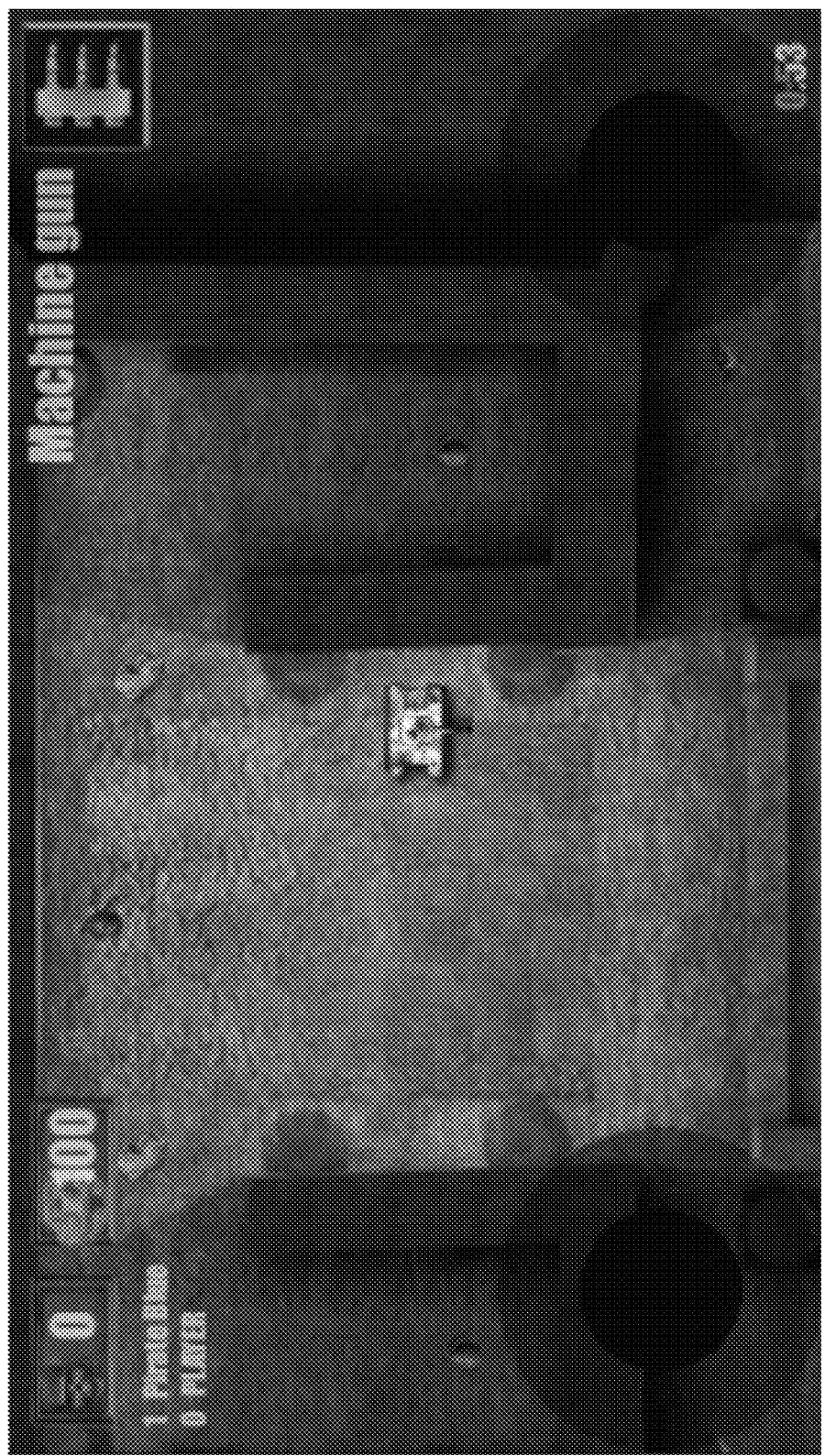
Figure 10B:
Figure 10C:
Figure 10D:
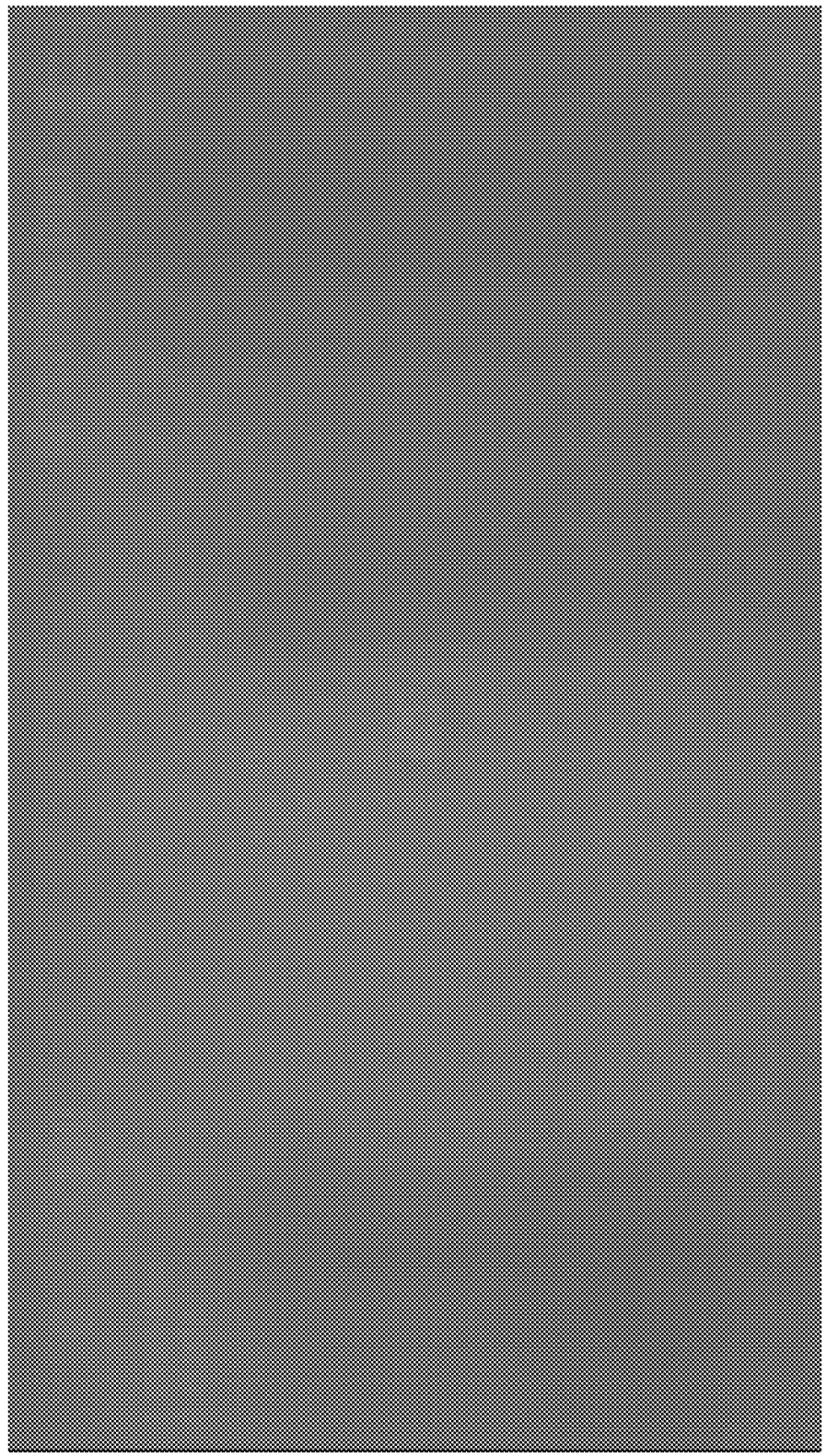
Figure 10E:
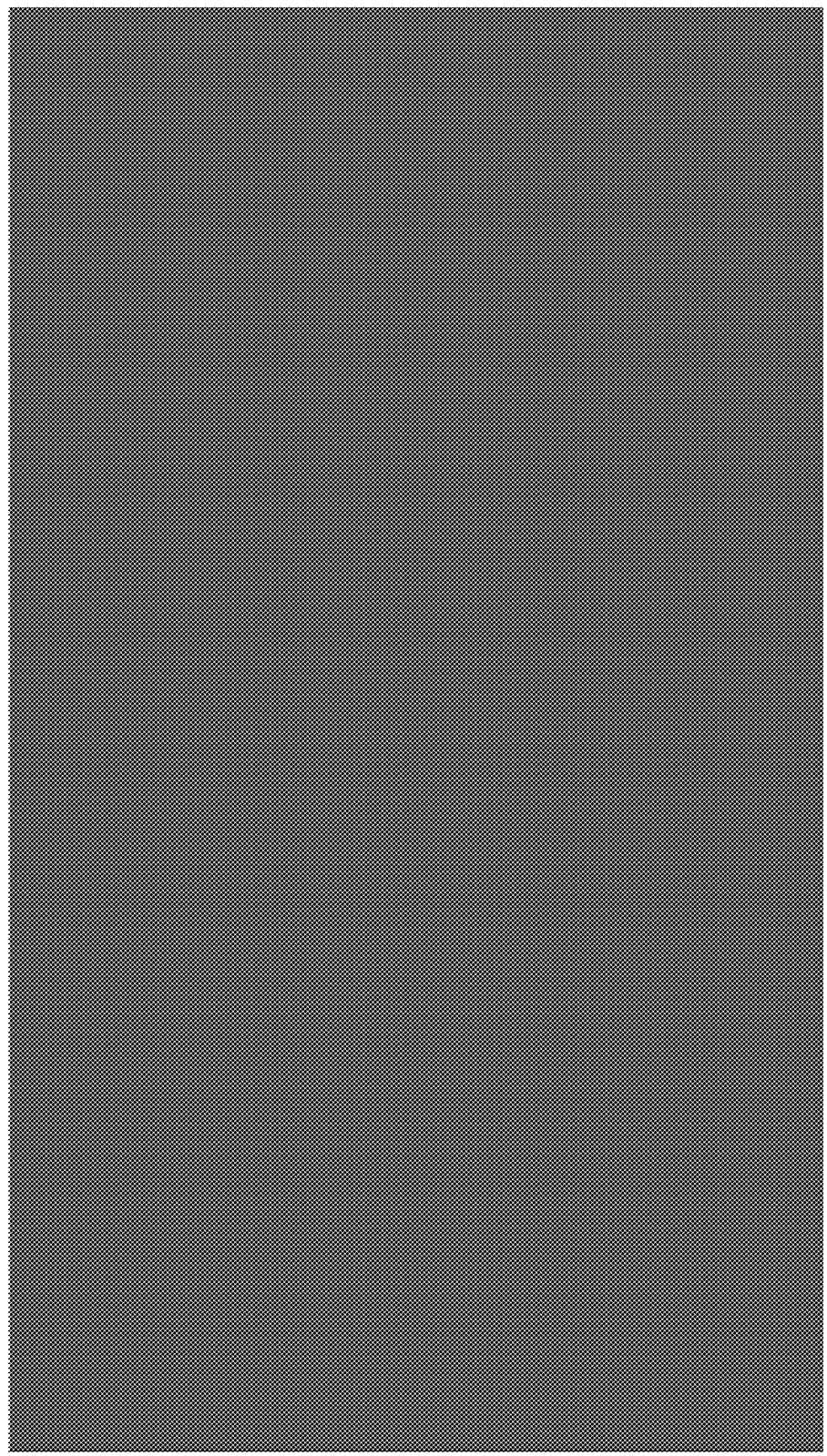

FIGS. 10A-10E illustrate another exemplary embodiment in which a gray overlay screen progressively obfuscates the visual display of a gaming application executing on processor 102 as the angle of inclination of system 100 increases through a predetermined angular range of twenty degrees. FIG. 10A illustrates the gray overlay screen at zero percent opacity. FIG. 10B illustrates the gray overlay screen at about five percent opacity. FIG. 10C illustrates the gray overlay screen at about fifty percent opacity. FIG. 10D illustrates the gray overlay screen at about ninety-five percent opacity. FIG. 10E illustrates the gray overlay screen at one hundred percent opacity. In an embodiment, although the gray overlay screen is one hundred percent opaque and prevents the display of visual information, the underlying application (e.g., gaming application) continues unimpeded.

Although the embodiments described above assumed than a ninety degree angle of inclination of system 100 was most preferable and a zero degree angle of inclination of system 100 was least preferable because the user was sitting or standing, one having ordinary skill in the art will understand that the ninety degree range may be altered for other user positions. For example, when the user is lying on his or her back, a one hundred eighty degree angle of inclination of system 100 is most preferable and a ninety degree angle of inclination of system 100 is least preferable. One having ordinary skill in the art will understand how to alter the embodiments described herein, which assumed a 0 degree to 90 degree range, to accommodate these other user positions.

Aspects of the invention described herein are designed to be employed with uses of system 100 (e.g., a mobile device) involving visual engagement and does not interfere with general audio uses, such as voice calls, music playing, and the like.

A system embodying aspects of the invention includes an electronic visual display (e.g., electronic visual display 106), an orientation sensor (e.g., sensor 108), a processor (e.g., processor 102), and a memory device (e.g., memory device 104). The processor is communicatively coupled to the electronic visual display and the orientation sensor. The memory device stores processor-executable instructions. When executed by the processor, the instructions configure to the processor to receive (402) signals indicative of an angle of inclination of the system from the orientation sensor and compare (404) the angle of inclination of the system with a predetermined angular range. The predetermined angular range corresponds to a less desirable behavior (e.g., cervical spinal posture) of a user of the system. The instructions also configure the processor to determine (406) the user has the less desirable behavior when the angle of inclination of the system is within the predetermined angular range. And the instructions configure the processor to alter (408) a display of visual information by the electronic visual display in real time when the user of the system has the incorrect behavior.

In another embodiment, a method in accordance with an aspect of the invention includes a processor of a mobile computing device executing processor-executable instructions. The executing instructions receive (402) signals indicative of an angle of inclination of a mobile computing device from an orientation sensor. The executing instructions compare (404) the angle of inclination of the mobile computing device with a predetermined angular range. The predetermined angular range corresponds to a less desirable behavior (e.g., cervical spinal posture) of a user of the mobile computing device. The executing instructions further determine (406) the user has the less desirable behavior when the angle of inclination of the mobile computing device is within the predetermined angular range and alter (408) a display of visual information on an electronic visual display of the mobile computing device in real time when the user has the less desirable behavior.

In yet another embodiment, a system in accordance with an aspect of the invention includes a display device (e.g., electronic visual display 106), an orientation sensor (e.g., sensor 108), a processor (e.g., processor 102), and a memory device (e.g., memory device 104). The processor is communicatively coupled to the display device and the orientation sensor. The memory device stores processor-executable instructions. When executed by the processor, the instructions configure to the processor to receive (402) signals indicative of an angle of inclination of the system from the orientation sensor. The angle of inclination of the system is representative of an angle of inclination of a cervical spine of a user of the system. The instructions further configure the processor to compare (404) the angle of inclination of the cervical spine of the user with a predetermined angular range. And the instructions configure the processor to alter (408) a display of visual information by the display device in real time when the angle of inclination of the cervical spine of the user is within the predetermined angular range.

The exemplary processor-executable instructions below monitor and track a spinal posture of a user and, in an embodiment, alter a display of visual information on an electronic visual display based on the user's posture as further described herein when executed by a processor.

```
@JsonAdapter(BlurEffect.Deserializer.class)
class BlurEffect extends OverlayEffect {
    @ColorInt
    private final int color;
    private final int minAlpha;
    private final int maxAlpha;
    private BlurEffect(int minAngle, int maxAngle, @ColorInt int color, int minAlpha, int maxAlpha) {
        super(minAngle, maxAngle);
        this.color = color;
        this.minAlpha = minAlpha;
        this.maxAlpha = maxAlpha;
    }
    @NonNull
    @Override
    protected View createOverlayView( ) {
        return new BlurView(AppContext.get( ));
    }
    @Override
    protected void onAngleChange(int angle) {
        int alpha = minAlpha;
        if (maxAlpha > minAlpha) {
            double factor = 1 - (double) (angle - minAngle) / (maxAngle - minAngle);
            alpha += (maxAlpha - minAlpha) * factor;
        }
        overlayView.getBackground( ).setAlpha(alpha);
    }
    static class Deserializer implements JsonDeserializer<BlurEffect> {
        @Override
        public BlurEffect deserialize(JsonElement json, Type typeOfT, JsonDeserializationContext context)
                throws JsonParseException {
            JsonObject jsonObject = json.getAsJsonObject( );
            JsonObject paramsObject = jsonObject.getAsJsonObject("params");
            int minAngle = jsonObject.get("angleMin").getAsInt( );
            int maxAngle = jsonObject.get("angleMax").getAsInt( );
            int color = decodeColor(paramsObject.get("color").getAsString( ));
            int minAlpha = 0, maxAlpha = 255;
            if (paramsObject.has("minAlpha")) {
                minAlpha = Math.round(paramsObject.get("minAlpha").getAsFloat( ) * 255);
            }
            if (paramsObject.has("maxAlpha")) {
                maxAlpha = Math.round(paramsObject.get("maxAlpha").getAsFloat( ) * 255);
            }
            return new BlurEffect(minAngle, maxAngle, color, minAlpha, maxAlpha);
        }
    }
    private class BlurView extends View {
        private BlurView(Context context) {
            super(context);
            setBackgroundColor(color);
        }
    }
}
```

The exemplary processor-executable instructions below track user posture as further described herein when executed by a processor.

```
{
    "details": "Don't show any visualization",
    "title": "Track my posture only",
    "identifier": "0",
    "rules": [
        {
            "effect": "debug",
            "angleMax": 360,
            "params": {
                "fontSize": 24,
                "textAlign": 1,
                "fontName": "Helvetica",
                "textColor": "0 0 1 1"
            },
            "angleMin": 0
        },
        {
            "effect": "vibrate",
            "angleMax": 51,
            "params": {
                "delay": 1,
                "type": "double"
            },
            "angleMin": 0
        },
        {
            "effect": "vibrate",
            "angleMax": 56,
            "params": {
                "delay": 2,
                "type": "double"
            },
            "angleMin": 51
        },
        {
            "effect": "vibrate",
            "angleMax": 61,
            "params": {
                "delay": 3,
                "type": "double"
            },
            "angleMin": 56
        },
        {
            "effect": "vibrate",
            "angleMax": 66,
            "params": {
                "delay": 5,
                "type": "double"
            },
            "angleMin": 61
        },
        {
            "effect": "vibrate",
            "angleMax": 71,
            "params": {
                "delay": 5,
                "type": "single"
            },
            "angleMin": 66
        }
    ]
}
```

The exemplary processor-executable instructions below display a notification frame as further described herein when executed by a processor.

```
{
    "details": "Warn me with color frame around the screen",
    "title": "Show frame",
    "identifier": "1",
    "rules": [
```

```
{
    "effect": "debug",
    "angleMax": 360,
    "params": {
        "fontSize": 24,
        "textAlign": 1,
        "fontName": "Helvetica",
        "textColor": "0 0 1 1"
    },
    "angleMin": 0
},
{
    "effect": "frame",
    "angleMax": 65,
    "params": {
        "color": "1 0 0 1",
        "flashMin": 0,
        "thicknessMin": 7,
        "thicknessMax": 15
    },
    "angleMin": 0
},
{
    "effect": "frame",
    "angleMax": 75,
    "params": {
        "color": "1 1 0 1",
        "flashMin": 0,
        "thicknessMin": 7
    },
    "angleMin": 65
},
{
    "effect": "frame",
    "angleMax": 91,
    "params": {
        "color": "0 1 0 1",
        "flashMin": 0,
        "thicknessMin": 7
    },
    "angleMin": 75
},
{
    "effect": "vibrate",
    "angleMax": 51,
    "params": {
        "delay": 1,
        "type": "double"
    },
    "angleMin": 0
},
{
    "effect": "vibrate",
    "angleMax": 56,
    "params": {
        "delay": 2,
        "type": "double"
    },
    "angleMin": 51
},
{
    "effect": "vibrate",
    "angleMax": 61,
    "params": {
        "delay": 3,
        "type": "double"
    },
    "angleMin": 56
},
{
    "effect": "vibrate",
    "angleMax": 66,
    "params": {
        "delay": 5,
        "type": "double"
    },
    "angleMin": 61
},
{
    "effect": "vibrate",
    "angleMax": 71,
    "params": {
        "delay": 5,
        "type": "single"
    },
    "angleMin": 66
}
]
}
```

The exemplary processor-executable instructions below display a pulsing notification frame as further described herein when executed by a processor.

```
{
    "details": "Warn me with pulsing frame around the screen",
    "title": "Show pulsing frame",
    "identifier": "2",
    "rules": [
        {
            "effect": "debug",
            "angleMax": 360,
            "params": {
                "fontSize": 24,
                "textAlign": 1,
                "fontName": "Helvetica",
                "textColor": "0 0 1 1"
            },
            "angleMin": 0
        },
        {
            "effect": "frame",
            "angleMax": 55,
            "params": {
                "color": "1 0 0 1",
                "flashMin": 2,
                "thicknessMin": 7,
                "flashMax": 10,
                "thicknessMax": 15
            },
            "angleMin": 0
        },
        {
            "effect": "frame",
            "angleMax": 65,
            "params": {
                "color": "1 0 0 1",
                "flashMin": 1,
                "thicknessMin": 7
            },
            "angleMin": 55
        },
        {
            "effect": "frame",
            "angleMax": 69,
            "params": {
                "color": "1 1 0 1",
                "flashMin": 0,
                "thicknessMin": 7
            },
            "angleMin": 65
        },
        {
            "effect": "frame",
            "angleMax": 75,
            "params": {
                "color": "1 1 0 1",
                "flashMin": 0,
                "thicknessMin": 7
            },
            "angleMin": 69
        },
        {
            "effect": "frame",
            "angleMax": 81,
            "params": {
```

```
            "color": "0 1 0 1",
            "flashMin": 0,
            "thicknessMin": 7
        },
        "angleMin": 75
    },
    {
        "effect": "frame",
        "angleMax": 91,
        "params": {
            "color": "0 1 0 1",
            "flashMin": 0,
            "thicknessMin": 7
        },
        "angleMin": 81
    },
    {
        "effect": "vibrate",
        "angleMax": 51,
        "params": {
            "delay": 1,
            "type": "double"
        },
        "angleMin": 0
    },
    {
        "effect": "vibrate",
        "angleMax": 56,
        "params": {
            "delay": 2,
            "type": "double"
        },
        "angleMin": 51
    },
    {
        "effect": "vibrate",
        "angleMax": 61,
        "params": {
            "delay": 3,
            "type": "double"
        },
        "angleMin": 56
    },
    {
        "effect": "vibrate",
        "angleMax": 66,
        "params": {
            "delay": 5,
            "type": "double"
        },
        "angleMin": 61
    },
    {
        "effect": "vibrate",
        "angleMax": 71,
        "params": {
            "delay": 5,
            "type": "single"
        },
        "angleMin": 66
    }
    ]
}
```

The exemplary processor-executable instructions below obfuscate a display of visual information on an electronic visual display as further described herein when executed by a processor.

```
{
    "details": "Don't let me see anything with bad posture",
    "title": "Blur sceen out",
    "identifier": "3",
    "rules": [
        {
            "effect": "debug",
            "angleMax": 360,
            "params": {
                "fontSize": 24,
                "textAlign": 1,
                "fontName": "Helvetica",
                "textColor": "0 0 1 1"
            },
            "angleMin": 0
        },
        {
            "effect": "blur",
            "angleMax": 71,
            "params": {
                "style": 2,
                "color": "1 1 1 1"
            },
            "angleMin": 51
        },
        {
            "effect": "blur",
            "angleMax": 51,
            "params": {
                "style": 2,
                "color": "1 1 1 1",
                "maxAlpha": 1,
                "minAlpha": 1
            },
            "angleMin": 0
        },
        {
            "effect": "vibrate",
            "angleMax": 51,
            "params": {
                "delay": 1,
                "type": "double"
            },
            "angleMin": 0
        },
        {
            "effect": "vibrate",
            "angleMax": 56,
            "params": {
                "delay": 2,
                "type": "double"
            },
            "angleMin": 51
        },
        {
            "effect": "vibrate",
            "angleMax": 61,
            "params": {
                "delay": 3,
                "type": "double"
            },
            "angleMin": 56
        },
        {
            "effect": "vibrate",
            "angleMax": 66,
            "params": {
                "delay": 5,
                "type": "double"
            },
            "angleMin": 61
        },
        {
            "effect": "vibrate",
            "angleMax": 71,
            "params": {
                "delay": 5,
                "type": "single"
            },
            "angleMin": 66
        }
    ]
}
```

Embodiments of the present disclosure may comprise a special purpose computer including a variety of computer hardware, as described in greater detail below.

Embodiments within the scope of the present disclosure also include computer-readable media for carrying or having computer-executable instructions or data structures stored thereon. Such computer-readable media can be any available media that can be accessed by a special purpose computer. By way of example, and not limitation, such computer-readable media can comprise RAM, ROM, EEPROM, CD-ROM or other optical disk storage, magnetic disk storage, or other magnetic storage devices, or any other medium that can be used to carry or store desired program code means in the form of computer-executable instructions or data structures and that can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media. Computer-executable instructions comprise, for example, instructions and data which cause a general purpose computer, special purpose computer, or special purpose processing device to perform a certain function or group of functions.

The following discussion is intended to provide a brief, general description of a suitable computing environment in which aspects of the disclosure may be implemented. Although not required, aspects of the disclosure will be described in the general context of computer-executable instructions, such as program modules, being executed by computers in network environments. Generally, program modules include routines, programs, objects, components, data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represent examples of corresponding acts for implementing the functions described in such steps.

Those skilled in the art will appreciate that aspects of the disclosure may be practiced in network computing environments with many types of computer system configurations, including personal computers, hand-held devices, multi-processor systems, microprocessor-based or programmable consumer electronics, network PCs, minicomputers, mainframe computers, and the like. Aspects of the disclosure may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing aspects of the disclosure includes a special purpose computing device in the form of a conventional computer, including a processing unit, a system memory, and a system bus that couples various system components including the system memory to the processing unit. The system bus may be any of several types of bus structures including a memory bus or memory controller, a peripheral bus, and a local bus using any of a variety of bus architectures. The system memory includes read only memory (ROM) and random access memory (RAM). A basic input/output system (BIOS), containing the basic routines that help transfer information between elements within the computer, such as during start-up, may be stored in ROM. Further, the computer may include any device (e.g., computer, laptop, tablet, PDA, cell phone, mobile phone, a smart television, and the like) that is capable of receiving or transmitting an IP address wirelessly to or from the internet.

The computer may also include a magnetic hard disk drive for reading from and writing to a magnetic hard disk, a magnetic disk drive for reading from or writing to a removable magnetic disk, and an optical disk drive for reading from or writing to removable optical disk such as a CD-ROM or other optical media. The magnetic hard disk drive, magnetic disk drive, and optical disk drive are connected to the system bus by a hard disk drive interface, a magnetic disk drive-interface, and an optical drive interface, respectively. The drives and their associated computer-readable media provide nonvolatile storage of computer-executable instructions, data structures, program modules, and other data for the computer. Although the exemplary environment described herein employs a magnetic hard disk, a removable magnetic disk, and a removable optical disk, other types of computer readable media for storing data can be used, including magnetic cassettes, flash memory cards, digital video disks, Bernoulli cartridges, RAMs, ROMs, solid state drives (SSDs), and the like.

The computer typically includes a variety of computer readable media. Computer readable media can be any available media that can be accessed by the computer and includes both volatile and nonvolatile media, removable and non-removable media. By way of example, and not limitation, computer readable media may comprise computer storage media and communication media. Computer storage media include both volatile and nonvolatile, removable and non-removable media implemented in any method or technology for storage of information such as computer readable instructions, data structures, program modules or other data. Computer storage media are non-transitory and include, but are not limited to, RAM, ROM, EEPROM, flash memory or other memory technology, CD-ROM, digital versatile disks (DVD) or other optical disk storage, SSDs, magnetic cassettes, magnetic tape, magnetic disk storage or other magnetic storage devices, or any other medium which can be used to store the desired non-transitory information, which can accessed by the computer. Alternatively, communication media typically embody computer readable instructions, data structures, program modules or other data in a modulated data signal such as a carrier wave or other transport mechanism and includes any information delivery media.

Program code means comprising one or more program modules may be stored on the hard disk, magnetic disk, optical disk, ROM, and/or RAM, including an operating system, one or more application programs, other program modules, and program data. A user may enter commands and information into the computer through a keyboard, pointing device, or other input device, such as a microphone, joy stick, game pad, satellite dish, scanner, or the like. These and other input devices are often connected to the processing unit through a serial port interface coupled to the system bus. Alternatively, the input devices may be connected by other interfaces, such as a parallel port, a game port, or a universal serial bus (USB). A monitor or another display device is also connected to the system bus via an interface, such as video adapter 48. In addition to the monitor, personal computers typically include other peripheral output devices (not shown), such as speakers and printers.

One or more aspects of the disclosure may be embodied in computer-executable instructions (i.e., software), routines, or functions stored in system memory or non-volatile memory as application programs, program modules, and/or program data. The software may alternatively be stored remotely, such as on a remote computer with remote application programs. Generally, program modules include routines, programs, objects, components, data structures, etc. that perform particular tasks or implement particular abstract data types when executed by a processor in a computer or other device. The computer executable instructions may be stored on one or more tangible, non-transitory computer readable media (e.g., hard disk, optical disk, removable storage media, solid state memory, RAM, etc.) and executed by one or more processors or other devices. As will be appreciated by one of skill in the art, the functionality of the program modules may be combined or distributed as desired in various embodiments. In addition, the functionality may be embodied in whole or in part in firmware or hardware equivalents such as integrated circuits, application specific integrated circuits, field programmable gate arrays (FPGA), and the like.

The computer may operate in a networked environment using logical connections to one or more remote computers. The remote computers may each be another personal computer, a tablet, a PDA, a server, a router, a network PC, a peer device, or other common network node, and typically include many or all of the elements described above relative to the computer. The logical connections include a local area network (LAN) and a wide area network (WAN) that are presented here by way of example and not limitation. Such networking environments are commonplace in office-wide or enterprise-wide computer networks, intranets and the Internet.

When used in a LAN networking environment, the computer is connected to the local network through a network interface or adapter. When used in a WAN networking environment, the computer may include a modem, a wireless link, or other means for establishing communications over the wide area network, such as the Internet. The modem, which may be internal or external, is connected to the system bus via the serial port interface. In a networked environment, program modules depicted relative to the computer, or portions thereof, may be stored in the remote memory storage device. It will be appreciated that the network connections shown are exemplary and other means of establishing communications over wide area network may be used.

Preferably, computer-executable instructions are stored in a memory, such as the hard disk drive, and executed by the computer. Advantageously, the computer processor has the capability to perform all operations (e.g., execute computer-executable instructions) in real-time.

The order of execution or performance of the operations in embodiments illustrated and described herein is not essential, unless otherwise specified. That is, the operations may be performed in any order, unless otherwise specified, and embodiments may include additional or fewer operations than those disclosed herein. For example, it is contemplated that executing or performing a particular operation before, contemporaneously with, or after another operation is within the scope of aspects of the disclosure.

Embodiments may be implemented with computer-executable instructions. The computer-executable instructions may be organized into one or more computer-executable components or modules. Aspects of the disclosure may be implemented with any number and organization of such components or modules. For example, aspects of the disclosure are not limited to the specific computer-executable instructions or the specific components or modules illustrated in the figures and described herein. Other embodiments may include different computer-executable instructions or components having more or less functionality than illustrated and described herein.

When introducing elements of aspects of the disclosure or the embodiments thereof, the articles "a", "an", "the" and "said" are intended to mean that there are one or more of the elements. The terms "comprising", "including", and "having" are intended to be inclusive and mean that there may be additional elements other than the listed elements.

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

What is claimed is:

1. A system, comprising:
   an electronic visual display device configured to generate a visual display to be viewed by a user, wherein the electronic visual display device is positioned in front of the user for viewing of the visual display during use of the system by the user;
   an orientation sensor generating signals indicative of an angle of inclination of the system, wherein the angle of inclination of the system corresponds to a cervical spinal posture of the user during use of the system by the user;
   a processor, wherein the processor is communicatively coupled to the electronic visual display and the orientation sensor; and
   a memory device storing processor-executable instructions, wherein the instructions, when executed by the processor, configure the processor to:
   receive the signals indicative of the angle of inclination of the system from the orientation sensor,
   compare the angle of inclination of the system with a predetermined angular range,
   define the angle of inclination of the system as corresponding to the user having an incorrect cervical spinal posture during use of the system when the angle of inclination of the system is within the predetermined angular range, and
   alter the visual display by the electronic visual display device in real time in response to the angle of inclination of the system being within the predetermined angular range corresponding to the user of the system having the incorrect cervical spinal posture.

2. The system of claim 1, wherein said altering the visual display comprises obfuscating the visual display by the electronic visual display device.

3. The system of claim 2, wherein the obfuscation progressively increases as the angle of inclination of the system progresses through the predetermined angular range.

4. The system of claim 2, wherein the obfuscation comprises overlaying a gray screen atop the visual display.

5. The system of claim 4, wherein the gray screen has a continuously variable translucency ranging from transparent to opaque as a function of the angle of inclination of the system.

6. The system of claim 4, wherein the instructions, when executed by the processor, further configure the processor to continue executing at least one of an application and an operating system while the gray screen is overlaid atop the visual display.

7. The system of claim 2, wherein the obfuscation comprises overlaying a predetermined, user-defined image atop the visual display, wherein the image has a continuously variable translucency ranging from transparent to opaque as a function of the angle of inclination of the system.

8. The system of claim 7, wherein the instructions, when executed by the processor, further configure the processor to continue executing at least one of an application and an operating system while the image is overlaid atop the visual display.

9. The system of claim 1, wherein said altering the visual display comprises displaying a frame around the visual display and reducing an area of the visual display by a thickness of the frame.

10. The system of claim 1, wherein said altering the visual display comprises displaying a translucent frame around the visual display.

11. The system of claim 9, wherein the frame progressively changes colors as the angle of inclination of the system progresses through the predetermined angular range.

12. The system of claim 9, wherein the frame pulses when the angle of inclination of the system is at one or more predetermined angles.

13. The system of claim 9, wherein the system vibrates when the angle of inclination of the system is at one or more predetermined angles.

14. The system of claim 9, wherein the thickness of the frame progressively increases as the angle of inclination of the system progresses through the predetermined angular range.

15. The system of claim 1, wherein the instructions, when executed by the processor, further configure the processor to track the angle of inclination of the system and an amount of time at each said angle during execution of one or more applications.

16. The system of claim 1, wherein the orientation sensor is at least one of a gyroscope and an accelerometer.

17. The system of claim 1, wherein the predetermined angular range is set by at least one of the user of the system and a caretaker of the user of the system, and wherein the caretaker is at least one of a parent of the user, a guardian of the user, and a healthcare professional treating the user.

18. The system of claim 1, wherein the predetermined angular range comprises any twenty degree range between zero degrees and ninety degrees.

19. A method, comprising:
receiving, by a processor of a mobile computing device executing processor-executable instructions therefor, signals indicative of an angle of inclination of the mobile computing device from an orientation sensor thereof, the mobile computing device having an electronic visual display device configured to generate a visual display to be viewed by a user, the electronic visual display device configured to be positioned in front of the user for viewing of the visual display during use of the mobile computing device by the user, the angle of inclination of the mobile computing device corresponding to a cervical spinal posture of the user during use of the mobile computing device by the user;
comparing, by the processor executing processor-executable instructions therefor, the angle of inclination of the mobile computing device with a predetermined angular range;
defining, by the processor executing processor-executable instructions therefor, the angle of inclination of the mobile computing device as corresponding to the user having an incorrect cervical spinal posture during use of the mobile computing device when the angle of inclination of the mobile computing device is within the predetermined angular range; and
altering, by the processor executing processor-executable instructions therefor, the visual display by the electronic visual display device of the mobile computing device in real time in response to the angle of inclination of the mobile computing device being within the predetermined angular range corresponding to the user having the incorrect cervical spinal posture.

20. A computer readable storage device having processor readable instructions stored thereon including instructions that, when executed by a processor, implement a method of altering a visual display on an electronic visual display device, comprising:
receiving signals indicative of an angle of inclination of a mobile computing device from an orientation sensor thereof, the mobile computing device having the electronic visual display device configured to generate the visual display, the electronic visual display device configured to be positioned in front of the user for viewing of the visual display during use of the mobile computing device by the user, the angle of inclination of the mobile computing device corresponding to a cervical spinal posture of the user during use of the mobile computing device by the user;
comparing the angle of inclination of the mobile computing device with a predetermined angular range;
defining the angle of inclination of the mobile computing device as corresponding to the user having an incorrect cervical spinal posture during use of the mobile computing device when the angle of inclination of the mobile computing device is within the predetermined angular range; and
altering the visual display on the electronic visual display device of the mobile computing device in real time in response to the angle of inclination of the mobile computing device being within the predetermined angular range corresponding to the user having the incorrect cervical spinal posture.

* * * * *